(12) United States Patent
Kawamoto et al.

(10) Patent No.: US 12,167,832 B2
(45) Date of Patent: Dec. 17, 2024

(54) ENDOSCOPE HAVING A TREATMENT TOOL OUTLET PORT

(71) Applicant: FUJIFILM Corporation, Tokyo (JP)

(72) Inventors: Yuta Kawamoto, Kanagawa (JP); Keita Takahashi, Kanagawa (JP); Kota Ninomiya, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/705,398

(22) Filed: Mar. 28, 2022

(65) Prior Publication Data

US 2022/0304552 A1 Sep. 29, 2022

(30) Foreign Application Priority Data

Mar. 29, 2021 (JP) .................. 2021-055276

(51) Int. Cl.
*A61B 1/00* (2006.01)
*A61B 1/05* (2006.01)
*A61B 1/06* (2006.01)
*A61B 1/07* (2006.01)

(52) U.S. Cl.
CPC ...... *A61B 1/00087* (2013.01); *A61B 1/00045* (2013.01); *A61B 1/00096* (2013.01); *A61B 1/00163* (2013.01); *A61B 1/05* (2013.01); *A61B 1/0676* (2013.01); *A61B 1/07* (2013.01)

(58) Field of Classification Search
CPC .............. A61B 1/00045; A61B 1/0008; A61B 1/00087; A61B 1/00091; A61B 1/018; A61B 1/07
See application file for complete search history.

(56) References Cited

U.S. PATENT DOCUMENTS

| | | | | |
|---|---|---|---|---|
| 5,725,477 A | * | 3/1998 | Yasui | ................. A61B 1/00091 |
| | | | | 600/125 |
| 6,458,074 B1 | * | 10/2002 | Matsui | .................. A61B 1/018 |
| | | | | 600/106 |
| 2003/0040657 A1 | * | 2/2003 | Yamaya | ............. A61B 1/00147 |
| | | | | 600/106 |
| 2005/0272975 A1 | * | 12/2005 | McWeeney | ............ A61B 1/307 |
| | | | | 600/172 |

(Continued)

FOREIGN PATENT DOCUMENTS

| | | |
|---|---|---|
| JP | 2002330920 | 11/2002 |
| JP | 2003153851 | 5/2003 |

(Continued)

OTHER PUBLICATIONS

"Notice of Reasons for Refusal of Japan Counterpart Application", issued on Jul. 26, 2024, with English translation thereof, p. 1-p. 12.

*Primary Examiner* — Timothy J Neal
(74) *Attorney, Agent, or Firm* — JCIPRNET

(57) ABSTRACT

An observation window is mainly disposed in a distal end surface region positioned above a horizontal axis, a first treatment tool outlet port is mainly disposed in a distal end surface region positioned below the horizontal axis, and a position of a center of a front water supply port in a direction of a vertical axis is disposed between a position of a center of the observation window and a position of a center of the first treatment tool outlet port in the direction of the vertical axis.

13 Claims, 13 Drawing Sheets

(56) References Cited

U.S. PATENT DOCUMENTS

| | | | |
|---|---|---|---|
| 2005/0272977 A1* | 12/2005 | Saadat | A61B 1/04 600/114 |
| 2007/0260120 A1* | 11/2007 | Otawara | G02B 23/2476 600/156 |
| 2008/0086032 A1 | 4/2008 | Ichimura | |
| 2008/0188890 A1* | 8/2008 | Weitzner | A61B 1/00154 606/205 |
| 2009/0093681 A1* | 4/2009 | Ichimura | A61B 1/00096 600/178 |
| 2012/0016191 A1* | 1/2012 | Ito | A61B 1/0051 600/104 |
| 2017/0150873 A1 | 6/2017 | Tatebayashi | |
| 2018/0064315 A1* | 3/2018 | Furlong | A61B 1/31 |
| 2019/0104927 A1* | 4/2019 | Mizuno | A61B 1/0008 |

FOREIGN PATENT DOCUMENTS

| | | |
|---|---|---|
| JP | 2003305001 | 10/2003 |
| JP | 2004194740 | 7/2004 |
| JP | 2006034457 | 2/2006 |
| JP | 2008086664 | 4/2008 |
| JP | 2012110526 | 6/2012 |
| JP | 2014132964 | 7/2014 |
| WO | 2016181688 | 11/2016 |
| WO | WO-2021176570 A1 * | 9/2021 |

\* cited by examiner

FIG. 1
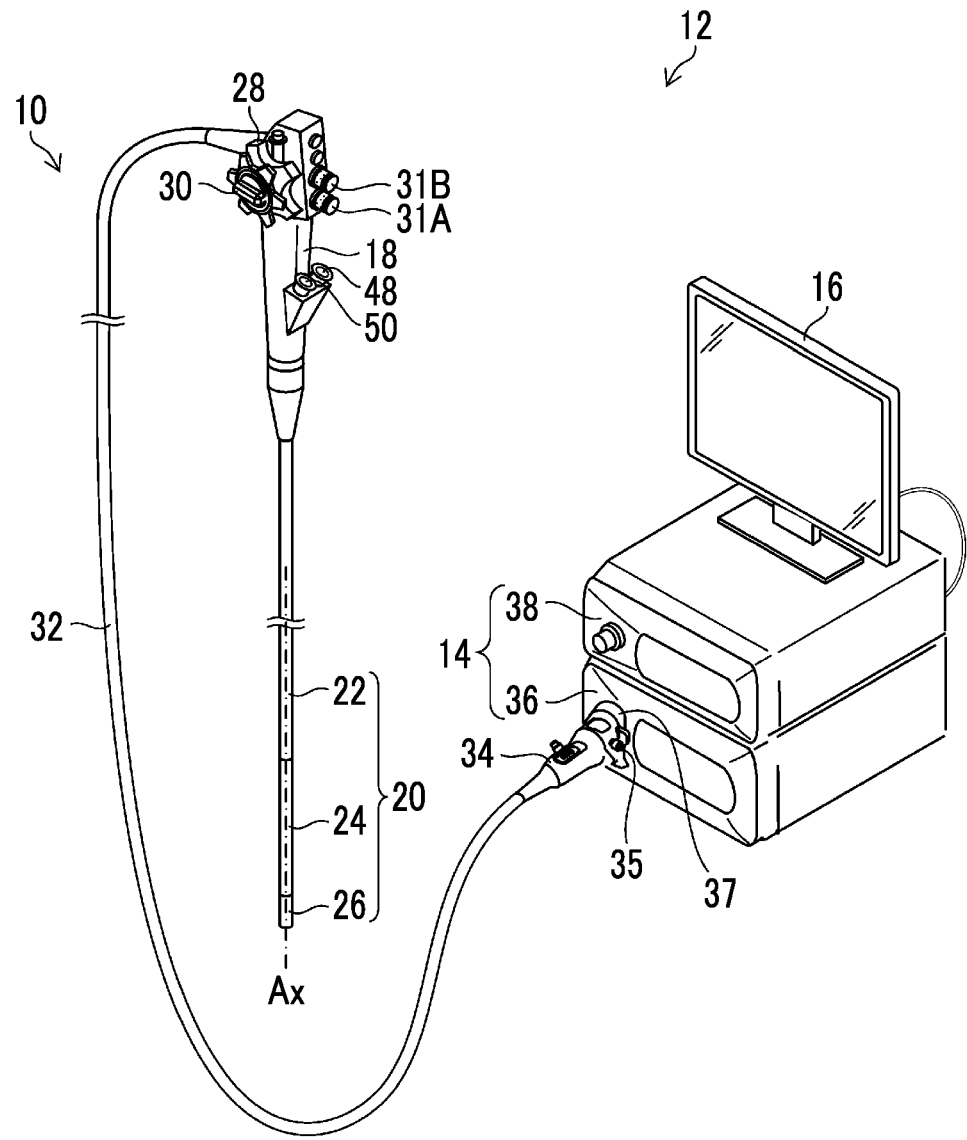
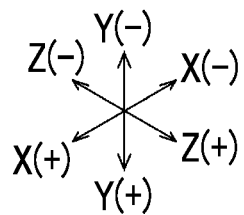

FIG. 2
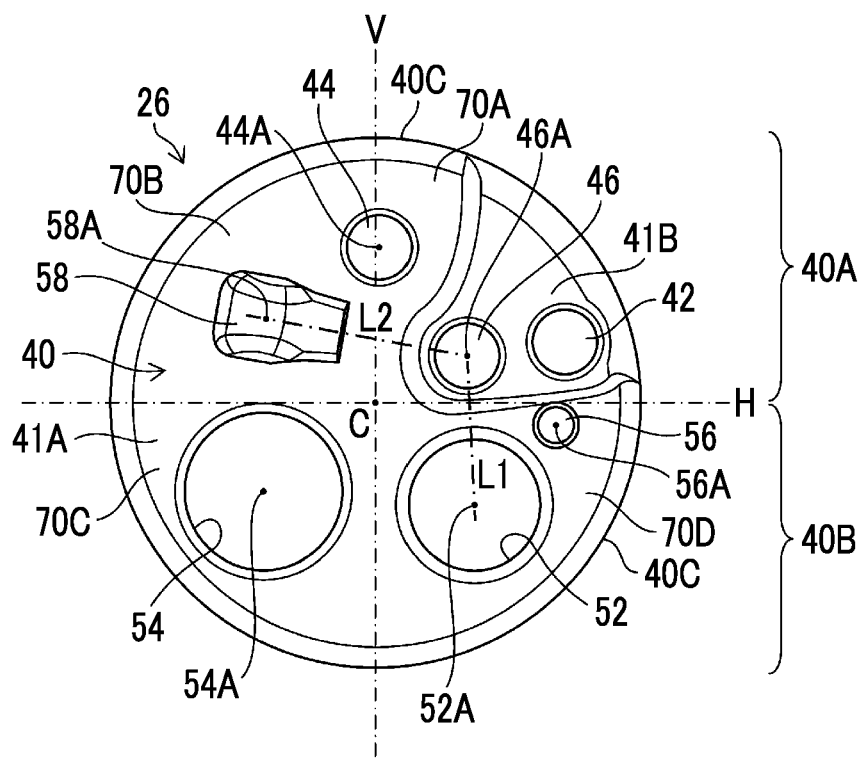
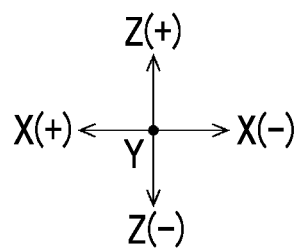

FIG. 3
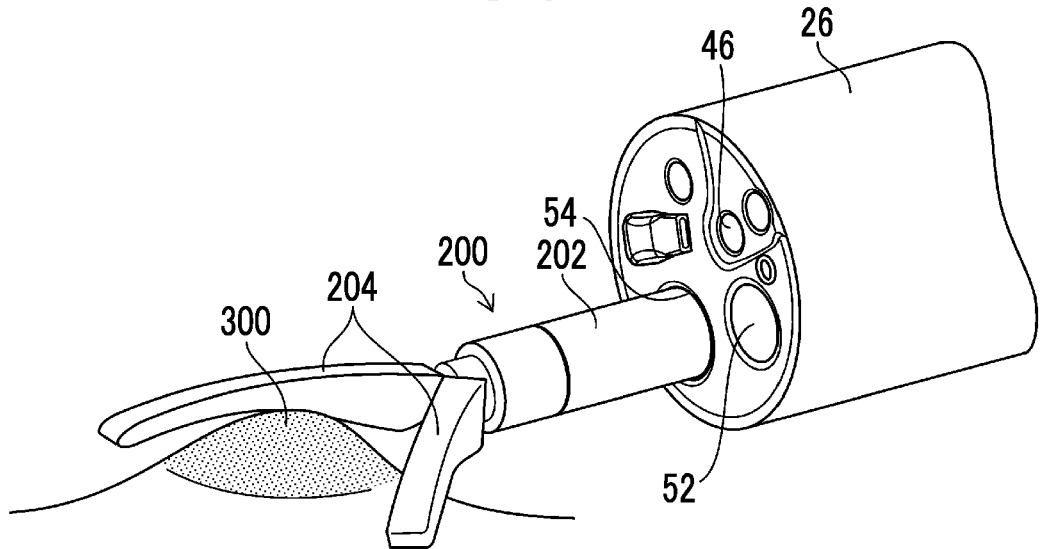
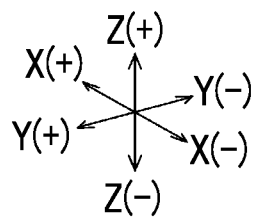
FIG. 4
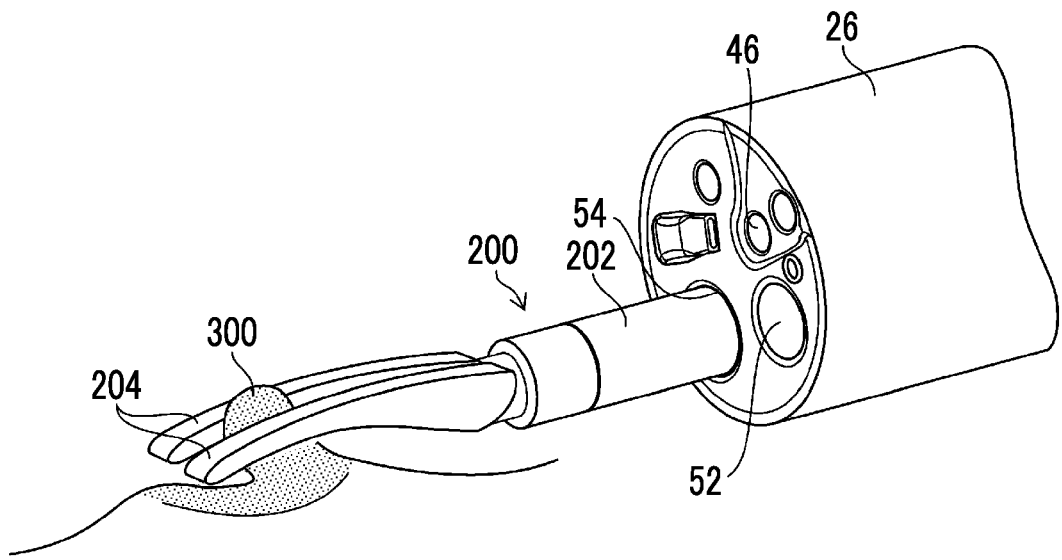
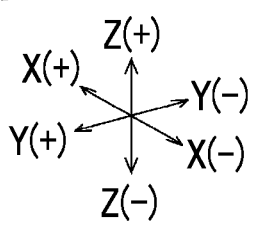

FIG. 5
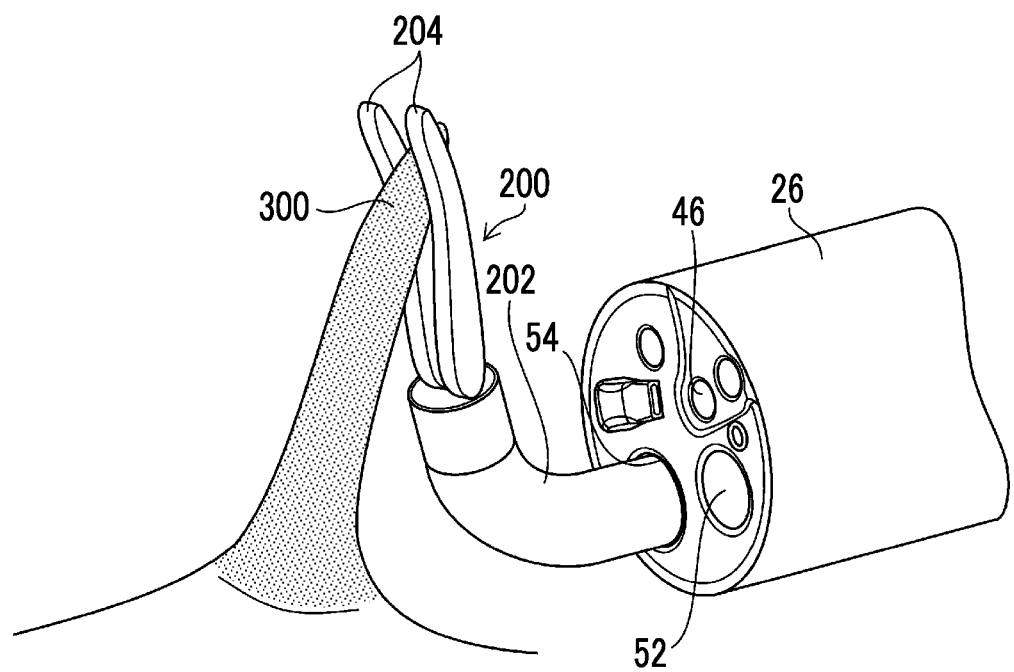
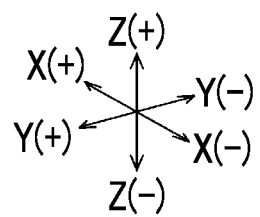

FIG. 6
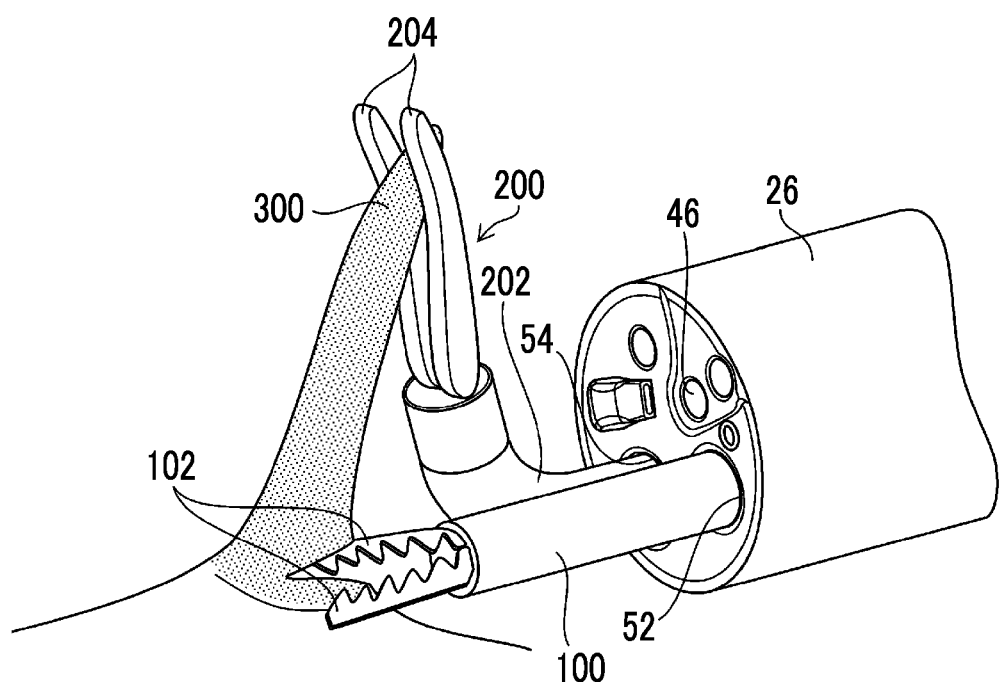
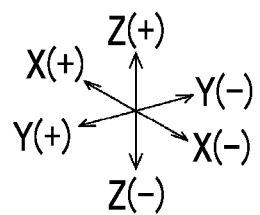

FIG. 7
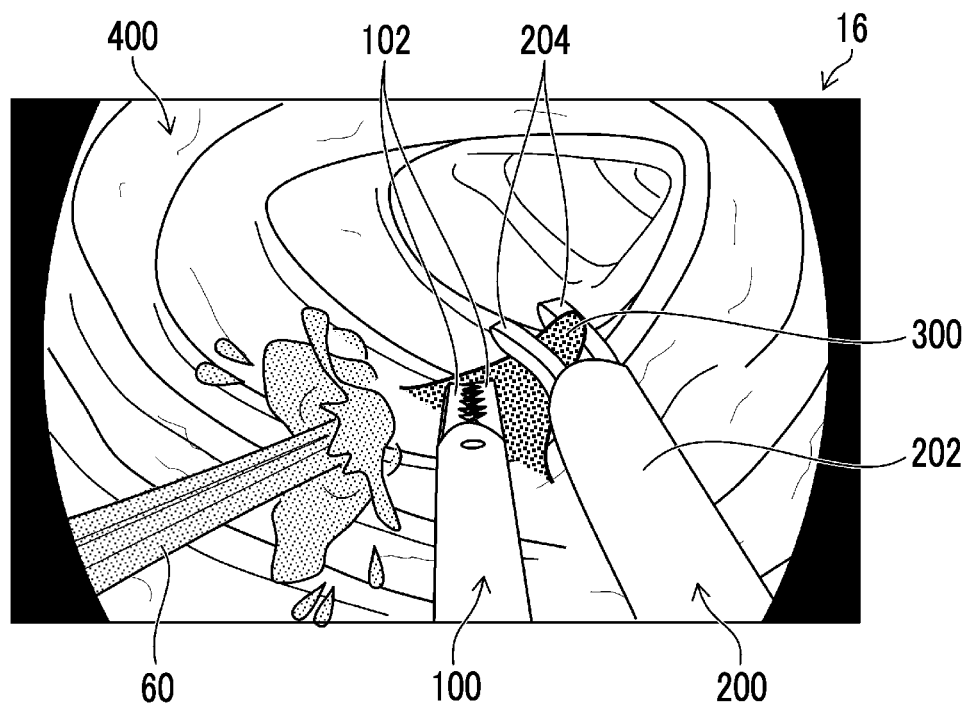
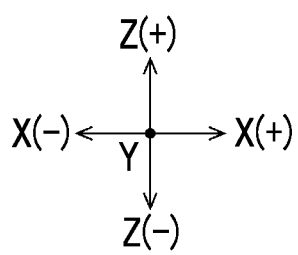
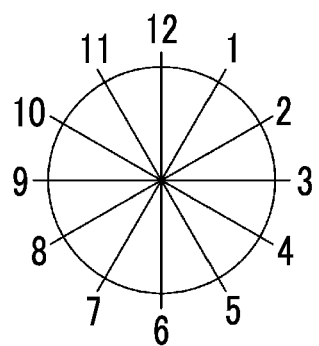

FIG. 8
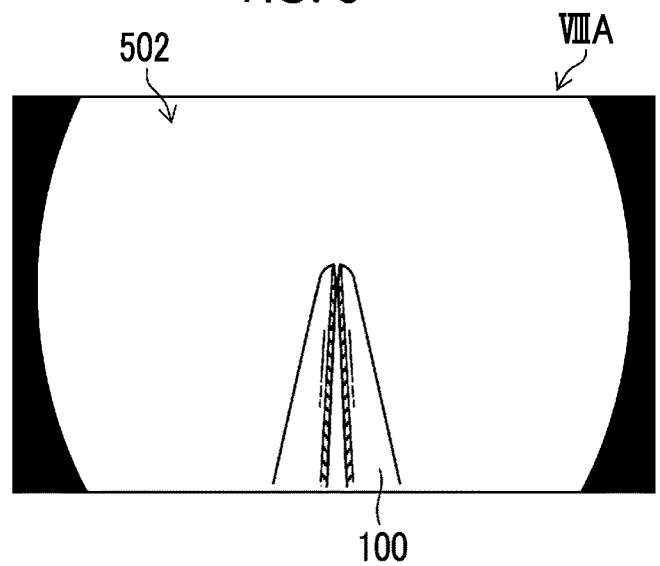
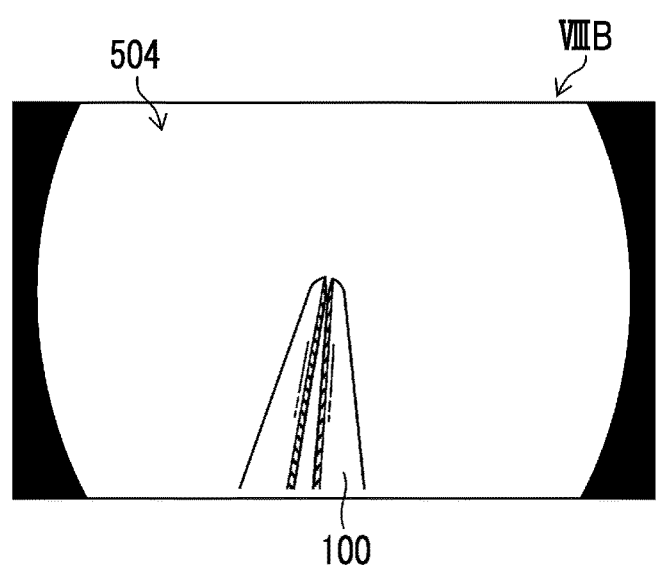
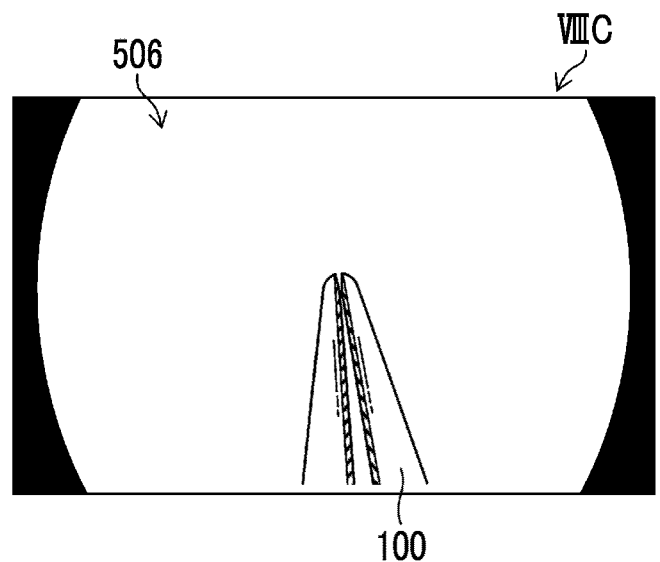

FIG. 12
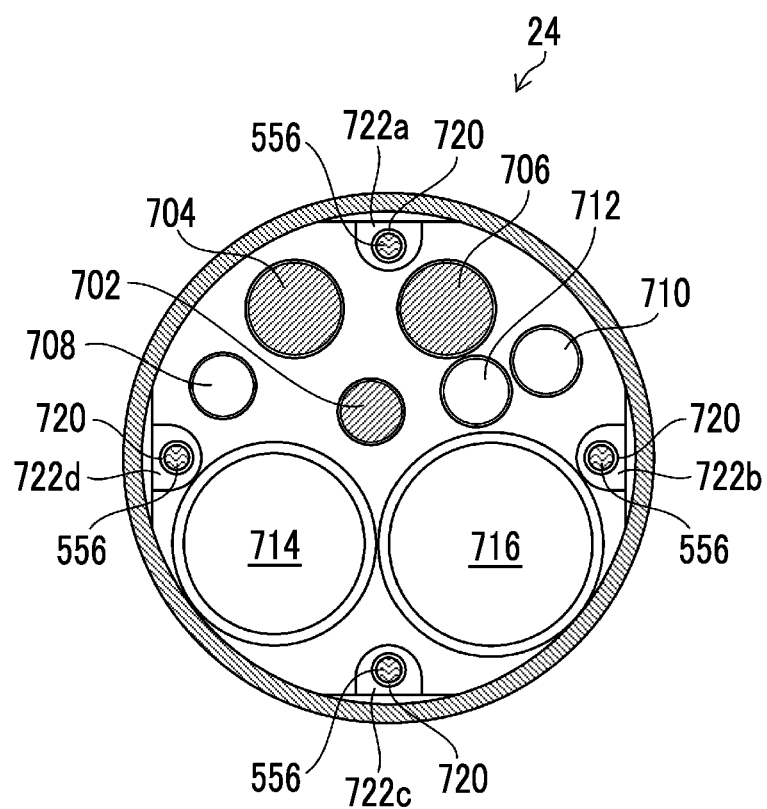
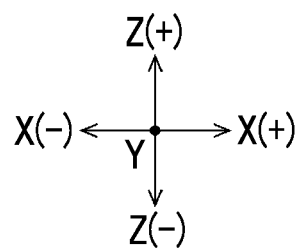

FIG. 13
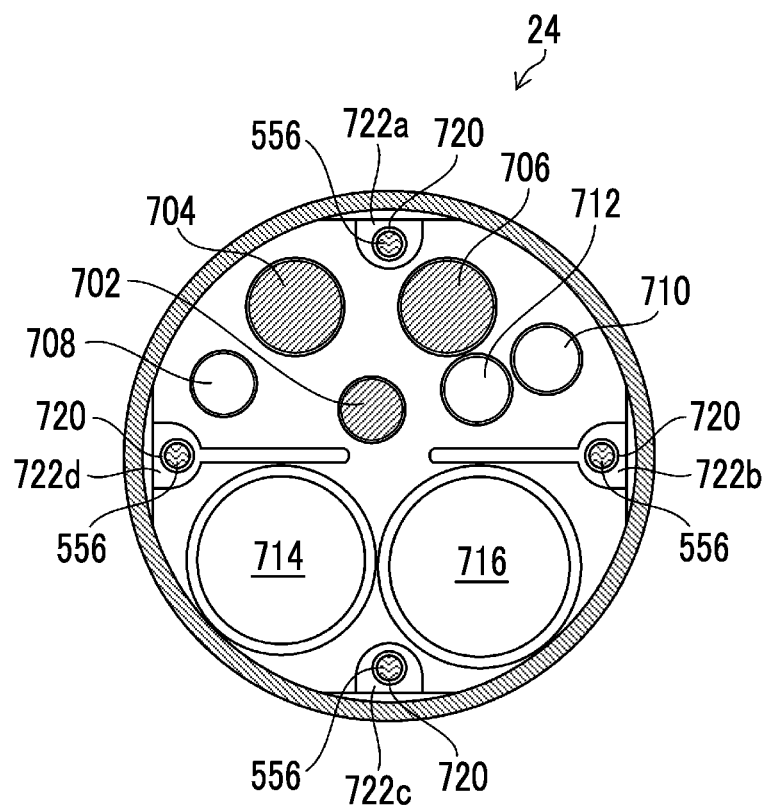
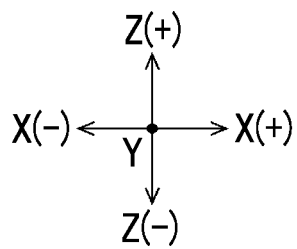

FIG. 14
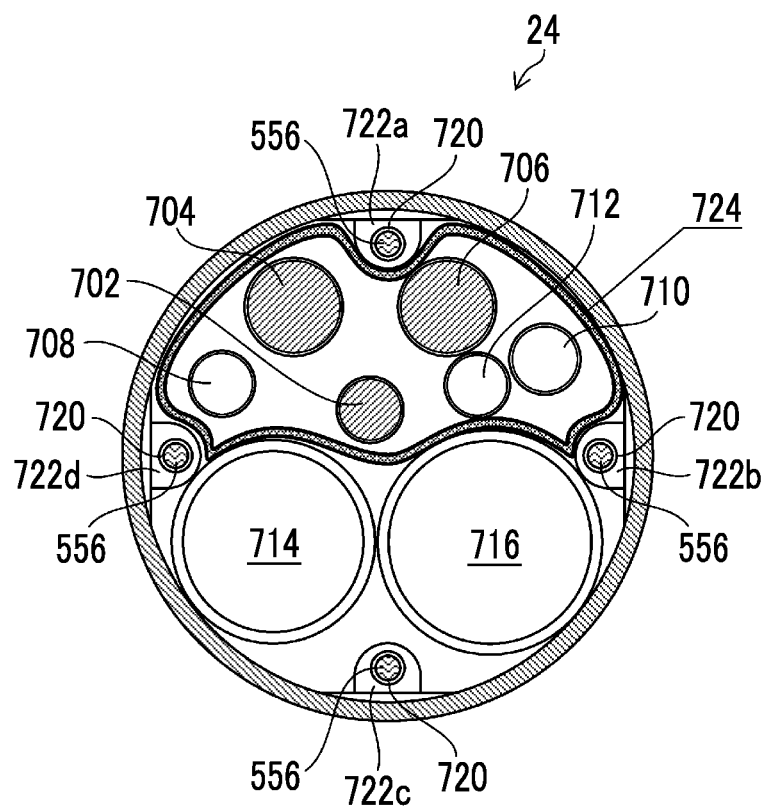
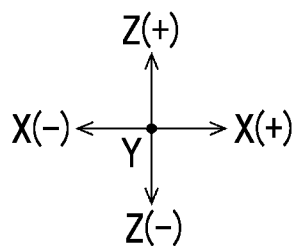

ENDOSCOPE HAVING A TREATMENT TOOL OUTLET PORT

CROSS-REFERENCE TO RELATED APPLICATION

The present application claims priority under 35 U.S.C § 119(a) to Japanese Patent Application No. 2021-055276 filed on Mar. 29, 2021, which is hereby expressly incorporated by reference, in its entirety, into the present application.

BACKGROUND OF THE INVENTION

1. Field of the Invention

The present invention relates to an endoscope and more particularly to an endoscope that includes a treatment tool outlet port at a distal end part of an insertion unit.

2. Description of the Related Art

In an endoscope, various treatment tools are introduced from a treatment tool inlet port provided on an operation unit and are led out of a treatment tool outlet port opened to a distal end part of the insertion unit, so that various treatments are performed on an object to be examined. Endoscopic submucosal dissection (ESD) is known as an example of the treatment.

JP2002-330920A discloses an endoscope in which different types of treatment tools are led out of two treatment tool outlet ports opened to a distal end part of an insertion unit to perform treatment.

The endoscope disclosed in JP2002-330920A includes a cutting treatment tool-protrusion port from which a cutting treatment tool for cutting body tissue protrudes and a capturing treatment tool-protrusion port from which a capturing treatment tool for capturing cut tissue protrudes, as the two treatment tool outlet ports. Further, the cutting treatment tool-protrusion port and the capturing treatment tool-protrusion port are opened and disposed at positions with an observation window interposed therebetween in the diagonal direction of a visual field mask. Furthermore, a washing water-jetting nozzle for jetting washing water is disposed at a position closer to the cutting treatment tool-protrusion port than an intermediate position between the cutting treatment tool-protrusion port and the capturing treatment tool-protrusion port. The washing water-jetting nozzle jets washing water in a direction substantially parallel to a direction in which a treatment tool protrudes from the cutting treatment tool-protrusion port.

SUMMARY OF THE INVENTION

In the endoscope disclosed in JP2002-330920A, the capturing treatment tool protruding from the capturing treatment tool-protrusion port is observed as an image appearing from the upper side in a screen and facing the center of the screen in the image of the inside of an object to be examined that is obtained through the observation window. For this reason, the capturing treatment tool may serve as an obstacle and may make it difficult for an operator who performs treatment while looking at an image to look at a lesion area. As a result, it may be difficult to accurately perform treatment that uses the treatment tool.

The present invention has been made in consideration of such circumstances, and provides an endoscope that allows treatment, which uses a treatment tool, to be performed accurately.

An endoscope according to an aspect of the present invention comprises an observation window that is provided on a distal end surface of an insertion unit bendable in an up/down direction and a left/right direction and is used to observe an inside of an object to be examined, a first treatment tool outlet port which is provided on the distal end surface and out of which a first treatment tool is capable of being led, and a front water supply port that is provided on the distal end surface and jets liquid to a portion to be observed in the object to be examined. In a case where an axis, which is parallel to the left/right direction, of two axes, which pass through a center of the distal end surface and are orthogonal to each other, is defined as a first axis and an axis thereof parallel to the up/down direction is defined as a second axis as the distal end surface is viewed from a front, the observation window is mainly disposed in a distal end surface region positioned above the first axis, the first treatment tool outlet port is mainly disposed in a distal end surface region positioned below the first axis, and a position of a center of the front water supply port in a direction of the second axis is disposed between a position of a center of the observation window and a position of a center of the first treatment tool outlet port in the direction of the second axis.

In the aspect of the present invention, it is preferable that, in a case where, among four divided regions into which the distal end surface is divided by the first axis and the second axis, an upper right divided region is defined as a first quadrant, an upper left divided region is defined as a second quadrant, a lower left divided region is defined as a third quadrant, and a lower right divided region is defined as a fourth quadrant, the observation window is mainly disposed in the first quadrant and the first treatment tool outlet port is mainly disposed in the fourth quadrant or the third quadrant.

In the aspect of the present invention, it is preferable that the front water supply port is disposed to be offset to an outer periphery of the distal end surface on a side opposite to the center of the distal end surface with respect to a line connecting the center of the observation window to the center of the first treatment tool outlet port.

In the aspect of the present invention, it is preferable that the front water supply port is mainly disposed in the fourth quadrant.

In the aspect of the present invention, it is preferable that the endoscope further comprises a second treatment tool outlet port which is provided on the distal end surface and out of which a second treatment tool is capable of being led, the first treatment tool outlet port is mainly disposed in the fourth quadrant, and the second treatment tool outlet port is mainly disposed in the third quadrant.

In the aspect of the present invention, it is preferable that the second treatment tool outlet port has a diameter larger than a diameter of the first treatment tool outlet port.

In the aspect of the present invention, it is preferable that the distal end surface includes a first surface and a second surface that protruding in a direction toward a distal end of the insertion unit from the first surface, the front water supply port is disposed on the first surface, and the observation window is disposed on the second surface.

In the aspect of the present invention, it is preferable that the endoscope further comprises a first illumination window provided on the second surface.

In the aspect of the present invention, it is preferable that, in a case where, among four divided regions into which the distal end surface is divided by the first axis and the second axis, an upper right divided region is defined as a first quadrant, an upper left divided region is defined as a second quadrant, a lower left divided region is defined as a third quadrant, and a lower right divided region is defined as a fourth quadrant, an air/water supply nozzle is provided in the second quadrant.

In the aspect of the present invention, it is preferable that the endoscope further comprises a second illumination window provided on the distal end surface, and the second illumination window is disposed to be offset to an outer periphery of the distal end surface on a side opposite to the center of the distal end surface with respect to a line connecting the center of the observation window to a center of the air/water supply nozzle.

In the aspect of the present invention, it is preferable that the second illumination window is disposed on the second axis.

According to the present invention, treatment using a treatment tool can be performed accurately.

BRIEF DESCRIPTION OF THE DRAWINGS

FIG. 1 is a diagram showing the configuration of an endoscope system comprising an endoscope according to an embodiment.

FIG. 2 is a front view of a distal end part of an insertion unit.

FIG. 3 is a diagram illustrating the procedure of a treatment method in ESD using the endoscope according to the embodiment.

FIG. 4 is a diagram illustrating the procedure of the treatment method in ESD using the endoscope according to the embodiment.

FIG. 5 is a diagram illustrating the procedure of the treatment method in ESD using the endoscope according to the embodiment.

FIG. 6 is a diagram illustrating the procedure of the treatment method in ESD using the endoscope according to the embodiment.

FIG. 7 is an example of a biological image displayed on a display.

FIG. 8 is a diagram showing observation images picked up by an observation optical system.

FIG. 12 is a cross-sectional view showing the internal structure of the bendable part.

FIG. 13 is a cross-sectional view showing the internal structure of a bendable part.

FIG. 14 is a cross-sectional view showing the internal structure of a bendable part.

DESCRIPTION OF THE PREFERRED EMBODIMENTS

Figure 9:
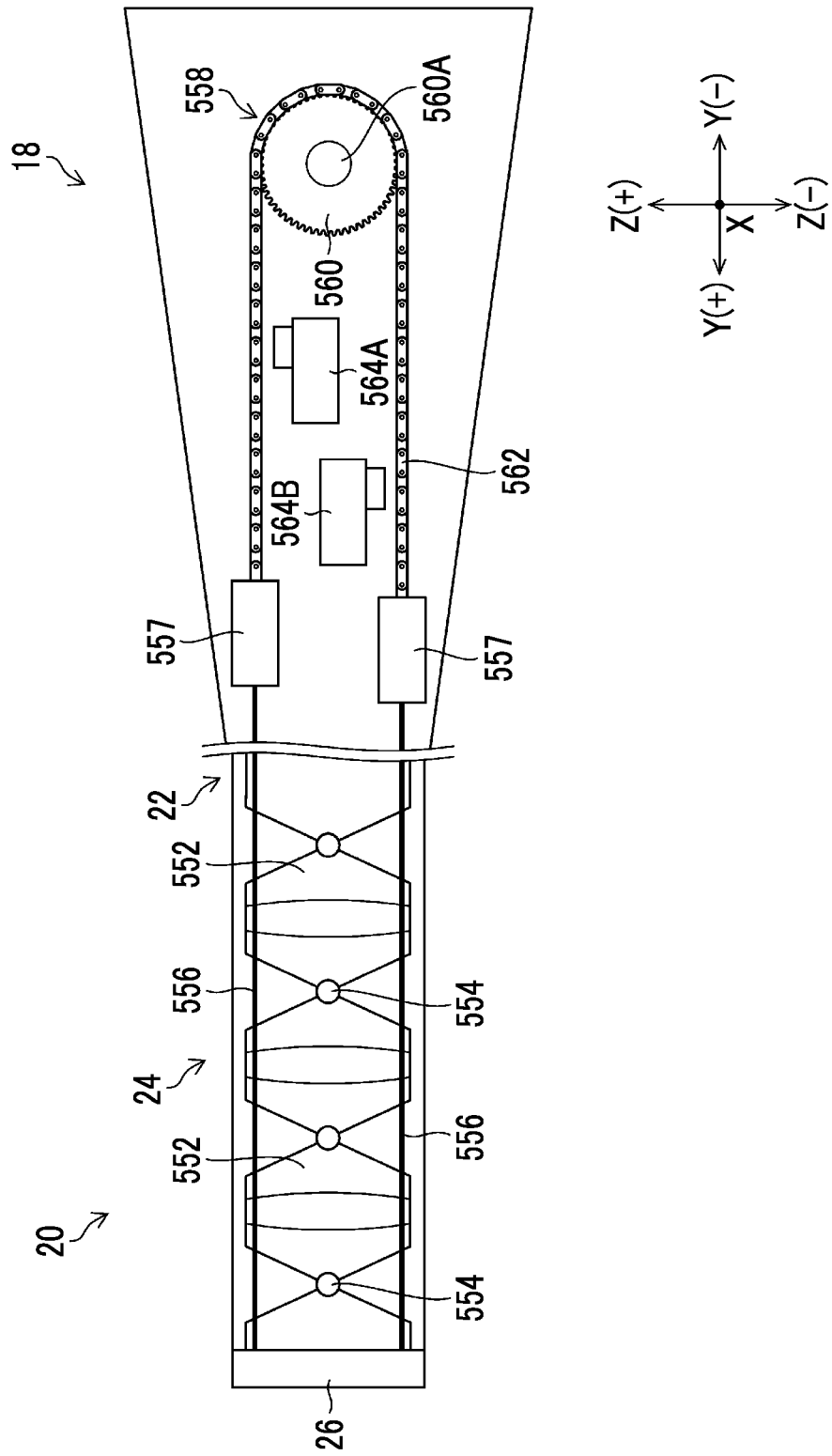
FIG. 9 is a schematic cross-sectional view of a hand operation unit and a bendable part.

An endoscope according to an embodiment of the present invention will be described below with reference to the accompanying drawings.

FIG. 1 is a diagram showing the configuration of an endoscope system 12 comprising an endoscope 10 according to an embodiment of the present invention. The endoscope system 12 comprises the endoscope 10, a processor device 14 for an endoscope, and a display 16.

The endoscope 10 comprises a hand operation unit 18 and an insertion unit 20 that is provided on the distal end side of the hand operation unit 18 and is to be inserted into an object to be examined.

The insertion unit 20 has a major axis Ax extending from a proximal end portion toward a distal end portion, and comprises a soft part 22, a bendable part 24, and a distal end part 26 that are arranged in this order from a proximal end side toward a distal end side.

A pair of angle knobs 28 and 30, which is used to perform an operation for bending the bendable part 24, is provided on the hand operation unit 18. The pair of angle knobs 28 and 30 is coaxially provided to be rotatable. The angle knobs 28 and 30 and the bendable part 24 are connected to each other by four angle wires (not shown) inserted into the soft part 22. Accordingly, these angle wires are pushed and pulled by an operation for rotating the angle knobs 28 and 30, so that the bendable part 24 is bent in an up/down direction and a left/right direction. Further, the hand operation unit 18 is provided with an air/water supply button 31A and a suction button 31B.

In this specification, a description will be provided using a three-dimensional Cartesian coordinate system having three axis directions (an X-axis direction, a Y-axis direction, and a Z-axis direction) orthogonal to each other. That is, in a case where a direction, in which the bendable part 24 faces in a case where the distal end part 26 is viewed from the hand operation unit 18 and the angle knob 28 for an operation in the up/down direction is moved rotationally in a UP direction, is defined as an upward direction, the upward direction is defined as a Z(+) direction and a downward direction opposite to the upward direction is defined as a Z(−) direction. Further, in a case where a direction, in which the bendable part 24 faces in a case where the angle knob 30 for an operation in the left/right direction is moved rotationally in an R direction, is defined as a right direction, the right direction is defined as an X(+) direction and a left direction is defined as an X(−) direction. Furthermore, a front side at that time (a direction corresponding to the distal end side in the direction of the major axis Ax) is defined as a Y(+) direction, and a rear side (a direction corresponding to the proximal end side in the direction of the major axis Ax) is defined as a Y(−) direction. The Y-axis direction including the Y(+) direction and the Y(−) direction is parallel to the direction of the major axis Ax.

A proximal end portion of a universal cable 32 is connected to the hand operation unit 18, and a distal end portion of the universal cable 32 is provided with a connector device 34. The connector device 34 is connected to the processor device 14 for an endoscope.

The processor device 14 for an endoscope comprises a light source device 36 and an image processing device 38. The light source device 36 is provided with a processor-side connector 37 to which the connector device 34 is to be connected. Further, the display 16, which displays an image processed by the image processing device 38, is connected to the image processing device 38. According to this endoscope system 12, light emitted from the light source device 36 is transmitted through an optical fiber cable (not shown) and is emitted to the front side (Y(+) direction) from illumination windows 42 and 44 provided on a distal end surface 40 (see FIG. 2) of the distal end part 26. Further, image light, which is incident from an observation window 46 (see FIG. 2) provided on the distal end surface 40, is received by, for example, an image pickup element (not shown) through an observation optical system (not shown) provided on the rear side (Y(−) direction) of the observation window 46. Then, electrical signals, which are photoelectrically converted by the image pickup element, are processed by the image processing device 38 and displayed in the screen of the display 16 as an image in the object to be examined (hereinafter, referred to as "biological image"). In the display 16, the up/down direction in which the bendable part 24 is to be bent is aligned with a vertical direction in the screen and the left/right direction in which the bendable part 24 is to be bent is aligned with a horizontal direction in the screen.

Further, the hand operation unit 18 shown in FIG. 1 is provided with a first treatment tool inlet port 48 into which a first treatment tool can be introduced and a second treatment tool inlet port 50 into which a second treatment tool can be introduced. Furthermore, a first treatment tool channel and a second treatment tool channel (not shown) are inserted into the insertion unit 20. The proximal end portion of the first treatment tool channel is connected to the first treatment tool inlet port 48, and the distal end portion thereof is connected to a first treatment tool outlet port 52 that is opened to the distal end surface 40 shown in FIG. 2. The proximal end portion of the second treatment tool channel is connected to the second treatment tool inlet port 50 shown in FIG. 1, and the distal end portion thereof is connected to a second treatment tool outlet port 54 that is opened to the distal end surface 40 shown in FIG. 2. For example, cutting treatment tools (for example, high-frequency forceps, an ESD knife, and biopsy forceps) for cutting (incising) body tissue are used as the first treatment tool. Further, a treatment tool having multiple functions is used as the second treatment tool. As such a treatment tool, there are, for example, grasping forceps having a grasping function and a bending function, an endoscopic suturing device having a suturing function, or the like. The above description is the outline of the endoscope 10.

Here, a forward-viewing endoscope in which a distal end part 26 of an insertion unit 20 is provided with an observation window 46 and treatment tool outlet ports (the first treatment tool outlet port 52 and the second treatment tool outlet port 54 in this embodiment) as in the endoscope 10 according to this embodiment requires the followings to allow treatment, which uses a treatment tool, to be accurately performed.

That is, an operator who operates the endoscope 10 leads a treatment tool out of the treatment tool outlet port to perform treatment for a lesion area while looking at the biological image displayed on the display 16. For this reason, it should be avoided that the treatment tool serves as an obstacle and makes it difficult for the lesion area to be seen in the biological image. Accordingly, in a case where components, such as the observation window 46, the first treatment tool outlet port 52, and the second treatment tool outlet port 54, provided on the distal end surface 40 of the distal end part 26 shown in FIG. 2 are disposed at suitable arrangement positions shown in FIG. 2, the endoscope 10 according to this embodiment allows treatment, which uses a treatment tool, to be accurately performed. An example of the suitable arrangement positions of the components will be described in detail below.

FIG. 2 is a front view of the distal end part 26. That is, FIG. 2 is a diagram in a case where the distal end surface 40 of the distal end part 26 is viewed toward a Y(−) side from a Y(+) side.

As shown in FIG. 2, the illumination windows 42 and 44, the observation window 46, the first treatment tool outlet port 52, the second treatment tool outlet port 54, a front water supply port 56, and an air/water supply nozzle 58 are provided at predetermined arrangement positions on the distal end surface 40 of the distal end part 26, respectively. Here, the illumination window 42 corresponds to a first illumination window of the present invention, and the illumination window 44 corresponds to a second illumination window of the present invention. Further, the observation window 46 corresponds to an observation window of the present invention, the first treatment tool outlet port 52 corresponds to a first treatment tool outlet port of the present invention, and the second treatment tool outlet port 54 corresponds to a second treatment tool outlet port of the present invention. Furthermore, the front water supply port 56 corresponds to a front water supply port of the present invention, and the air/water supply nozzle 58 corresponds to an air/water supply nozzle of the present invention.

The observation window 46 is a window that is used to observe the inside of an object to be examined positioned on the front side (Y(+) direction) of the distal end part 26 as already described, and the illumination windows 42 and 44 are disposed with the observation window 46 therebetween. Here, for example, in a case where the diameter of the distal end part 26 is in the range of 12.5 to 13.0 mm, each of the observation window 46 and the illumination windows 42 and 44 is formed with a diameter of, for example, about 1.5 to 2.0 mm.

The first treatment tool outlet port 52 is an opening portion out of which the already described cutting treatment tool (first treatment tool) can be led to the front side. The second treatment tool outlet port 54 is an opening portion out of which, for example, the already described grasping forceps (second treatment tool) can be led to the front side. The second treatment tool outlet port 54 is formed with a diameter of, for example, about 3.5 to 4.0 mm to make the grasping forceps, which have a diameter larger than the diameter of the cutting treatment tool, pass therethrough. That is, the diameter of the second treatment tool outlet port 54 is larger than the diameter (for example, about 3.0 to 3.5 mm) of the first treatment tool outlet port 52 through which only the cutting treatment tool may pass. The first treatment tool outlet port 52 also functions as a suction port that sucks liquid and the like in the object to be examined by the operation of the suction button 31B shown in FIG. 1.

The front water supply port 56 is an opening portion that jets liquid to a portion to be observed (for example, a lesion area) in the object to be examined, and is formed with a diameter of, for example, about 1.0 to 1.5 mm. The front water supply port 56 is connected to a water supply connector 35, which is provided on the connector device 34 (see FIG. 1), through a water supply tube (not shown). A water supply device (not shown) is connected to the water supply connector 35, and liquid is supplied to the front water supply port 56 through the water supply tube in a case where the water supply device is driven.

The air/water supply nozzle 58 is a nozzle that jets liquid and air mainly to the observation window 46. Liquid or air is selectively supplied to the air/water supply nozzle 58 in response to the operation of the air/water supply button 31A shown in FIG. 1.

Here, in a case where the distal end surface 40 is viewed from the front as shown in FIG. 2, an axis, which is parallel to the left/right direction, of two axes, which pass through a center C of the distal end surface 40 and are orthogonal to each other, is defined as a horizontal axis H and an axis thereof parallel to the up/down direction is defined as a vertical axis V. In this case, the observation window 46 is disposed in a distal end surface region 40A positioned above the horizontal axis H, and the first treatment tool outlet port 52 is disposed in a distal end surface region 40B positioned below the horizontal axis H. Further, with regard to the front water supply port 56, the position of a center 56A of the front water supply port 56 in the direction of the vertical axis V is disposed between the position of a center 46A of the observation window 46 and the position of a center 52A of the first treatment tool outlet port 52 in the direction of the vertical axis V. Here, the horizontal axis H corresponds to a first axis of the present invention and the vertical axis V corresponds to a second axis of the present invention.

Next, an example of a treatment method using the endoscope 10 according to the embodiment will be described with reference to FIGS. 3 to 6. The procedure of the treatment method in ESD is shown in FIGS. 3 to 6. Further, high-frequency forceps 100 including a pair of claws 102, which can be opened and closed, at distal end portions thereof as shown in FIG. 6 are used as the first treatment tool. The pair of claws 102 is opened and closed by an operation unit (not shown) for the high-frequency forceps 100. In a case where high-frequency current is made to flow between the pair of claws 102 in a state where the pair of claws 102 is closed and biological tissue is grasped by the pair of claws 102, the biological tissue is cauterized and incised.

Further, grasping forceps 200, which include a bendable part 202 and a pair of grasping parts 204 at the distal end portion thereof as shown in FIG. 3, are used as the second treatment tool. The bendable part 202 is bent by an operation unit (not shown) for the grasping forceps 200, and the pair of grasping parts 204 is opened and closed by the operation unit.

First, the operator orally inserts the insertion unit 20 of the endoscope 10 shown in FIG. 1 into the object to be examined. Then, in a case where the distal end part 26 is positioned on the lateral side of a lesion area 300 of a mucosal layer as shown in FIG. 3, the operator inserts the high-frequency forceps 100 (see FIG. 6) into the first treatment tool channel from the first treatment tool inlet port 48 of the endoscope 10 (see FIG. 1). After that, the operator inserts the grasping forceps 200 (see FIG. 3) into the second treatment tool channel from the second treatment tool inlet port 50, and leads the pair of grasping parts 204 and the bendable part 202 of the grasping forceps 200 forward out of the second treatment tool outlet port 54 as shown in FIG. 3. Then, the operator operates the operation unit (not shown) for the grasping forceps 200 to grasp the lesion area 300 by the pair of grasping parts 204 as shown in FIGS. 3 and 4.

Next, as shown in FIG. 5, the operator operates the operation unit (not shown) for the grasping forceps 200 to bend the bendable part 202 upward (Z(+) direction). Accordingly, the pair of grasping parts 204 is elevated, so that the lesion area 300 grasped by the pair of grasping parts 204 is lifted up.

Next, in a state where the lesion area 300 is lifted up as shown in FIG. 5, the operator leads the high-frequency forceps 100, which are inserted into the first treatment tool channel, to the front side out of the first treatment tool outlet port 52 as shown in FIG. 6. Then, the operator advances the pair of claws 102 of the high-frequency forceps 100 to the lower portion of the lesion area 300 to incise the lower portion of the lesion area 300 by the pair of claws 102. After that, after the lesion area 300 is completely incised, the operator pulls the grasping forceps 200 to the Y(−) side to take the lesion area 300 out of the endoscope 10 in a state where the lesion area 300 is grasped by the pair of grasping parts 204. The above description is an example of the treatment method in ESD.

FIG. 7 shows an example of a biological image 400 displayed on the display 16 in the treatment. In the description of the biological image 400 shown in FIG. 7, a so-called clock position, which is represented from 1 o'clock to 12 o'clock, will be used in addition to the up/down (Z axis) and the left/right (X axis).

According to the biological image 400 shown in FIG. 7, the high-frequency forceps 100 led out of the first treatment tool outlet port 52 (see FIG. 2) are observed as an image facing the lesion area 300, which is positioned at the center of the screen, from the position of about 6 o'clock on the lower side in the screen. That is, the endoscope 10 according to the embodiment has configuration in which the observation window 46 is disposed in the distal end surface region 40A positioned above the horizontal axis H and the first treatment tool outlet port 52 is disposed in the distal end surface region 40B positioned below the horizontal axis H as shown in FIG. 2. Specifically, in a case where the distal end surface 40 of the endoscope 10 is divided into four regions by the horizontal axis H and the vertical axis V, an upper right divided region is defined as a first quadrant 70A, an upper left divided region is defined as a second quadrant 70B, a lower left divided region is defined as a third quadrant 70C, and a lower right divided region is defined as a fourth quadrant 70D among the divided regions, the endoscope 10 according to the embodiment has configuration in which the observation window 46 is disposed in the first quadrant 70A and the first treatment tool outlet port 52 is disposed in the fourth quadrant 70D. Accordingly, the high-frequency forceps 100 led out of the first treatment tool outlet port 52 (see FIG. 2) are observed as an image facing the lesion area 300, which is positioned at the center of the screen, from the position of about 6 o'clock on the lower side in the screen.

Further, according to the biological image 400 shown in FIG. 7, liquid 60 jetted from the front water supply port 56 (see FIG. 2) is observed as an image facing the lesion area 300, which is positioned at the center of the screen, from the position of 7 to 8 o'clock on the lower left side in the screen. That is, the endoscope 10 according to the embodiment has configuration in which the position of the center 56A of the front water supply port 56 in the direction of the vertical axis V is disposed between the position of the center 46A of the observation window 46 and the position of the center 52A of the first treatment tool outlet port 52 in the direction of the vertical axis V. Specifically, the endoscope 10 according to the embodiment has configuration in which the front water supply port 56 is disposed to be offset to an outer periphery 40C of the distal end surface 40 on a side opposite to the center C of the distal end surface 40 with respect to a line L1 connecting the center 46A of the observation window 46 to the center 52A of the first treatment tool outlet port 52. Accordingly, the liquid 60 jetted from the front water supply port 56 is observed as an image facing the lesion area 300, which is positioned at the center of the screen, from the position of 7 to 8 o'clock on the lower left side in the screen of FIG. 7.

Here, a comparative example, which is contrasted with the endoscope 10 according to the embodiment, will be briefly described. For example, in a case where a treatment tool outlet port and a front water supply port are disposed in the distal end surface region positioned above the observation window in the direction of the vertical axis V shown in FIG. 2, a treatment tool led out of the treatment tool outlet port is observed as an image facing the center of a screen from the position of, for example, 11 to 1 o'clock on the upper side in the screen in a biological image displayed on the display. For this reason, the treatment tool may serve as an obstacle and may make it difficult for an operator who performs treatment while looking at the biological image 400 to look at a lesion area (that is, the lesion area is hidden by the treatment tool). Further, the treatment tool may serve as an obstacle and may also make it difficult for the operator to see whether or not liquid jetted from the front water supply port is accurately sprayed on the lesion area. As a result, it may be difficult to accurately perform treatment, which uses a treatment tool, in the comparative example.

In contrast, the endoscope 10 according to the embodiment has configuration in which the first treatment tool outlet port 52 is disposed in the distal end surface region positioned below the observation window 46. Specifically, the endoscope 10 according to the embodiment has configuration in which the observation window 46 is disposed in the distal end surface region 40A positioned above the horizontal axis H and the first treatment tool outlet port 52 is disposed in the distal end surface region 40B positioned below the horizontal axis H, and more specifically has configuration in which the observation window 46 is disposed in the first quadrant 70A and the first treatment tool outlet port 52 is disposed in the fourth quadrant 70D. Accordingly, as shown in FIG. 7, the high-frequency forceps 100 are observed as an image facing the lesion area 300, which is positioned at the center of the screen, from the position of about 6 o'clock on the lower side in the screen. As a result, in a case where the operator performs treatment while observing the lesion area 300 in the biological image 400, the high-frequency forceps 100 do not serve as an obstacle and the operator can accurately perform treatment, which uses the high-frequency forceps 100, while observing the lesion area 300.

Further, the endoscope 10 according to the embodiment has configuration in which the front water supply port 56 is disposed in the distal end surface region positioned below the observation window 46. Specifically, the endoscope 10 according to the embodiment has configuration in which the position of the center 56A of the front water supply port 56 in the direction of the vertical axis V is disposed between the position of the center 46A of the observation window 46 and the position of the center 52A of the first treatment tool outlet port 52 in the direction of the vertical axis V, and more specifically has configuration in which the front water supply port 56 is disposed to be offset to the outer periphery 40C of the distal end surface 40 on a side opposite to the center C of the distal end surface 40 with respect to the line L1 connecting the center 46A of the observation window 46 to the center 52A of the first treatment tool outlet port 52. Accordingly, the liquid 60 and the high-frequency forceps 100 are displayed in the biological image 400 without overlapping with each other. As a result, it is easy to see whether or not the liquid 60 jetted from the front water supply port 56 is accurately sprayed on the lesion area.

Therefore, according to the endoscope 10 of the embodiment, since the observation window 46 is disposed in the distal end surface region 40A positioned above the horizontal axis H, the first treatment tool outlet port 52 is disposed in the distal end surface region 40B positioned below the horizontal axis H, and the position of the center 56A of the front water supply port 56 in the direction of the vertical axis V is disposed between the position of the center 46A of the observation window 46 and the position of the center 52A of the first treatment tool outlet port 52 in the direction of the vertical axis V, treatment using the high-frequency forceps 100 can be performed accurately.

Configuration in which the observation window 46 and the first treatment tool outlet port 52 are completely included in corresponding regions corresponding thereto (that is, the distal end surface region 40A and the distal end surface region 40B), respectively has been shown in FIG. 2, but the configuration of the endoscope is not necessarily limited thereto. The observation window 46 and the first treatment tool outlet port 52 may be mainly disposed in the corresponding regions corresponding thereto, respectively. Likewise, configuration in which the observation window 46, the first treatment tool outlet port 52, and the second treatment tool outlet port 54 are completely included in corresponding regions corresponding thereto (that is, the first quadrant 70A, the fourth quadrant 70D, and the third quadrant 70C), respectively has been shown in FIG. 2, but the configuration of the endoscope is not necessarily limited thereto. The observation window 46, the first treatment tool outlet port 52, and the second treatment tool outlet port 54 may be mainly disposed in the corresponding regions corresponding thereto, respectively.

Here, the above-mentioned "mainly disposed" means a case where the majority (half or more) of a component (for example, the observation window 46) as an object to be disposed is included in the corresponding region corresponding thereto (the distal end surface region 40A in the case of the observation window 46). That is, the configuration of the endoscope is not limited to the configuration in which the component is completely included in the corresponding region corresponding thereto, and configuration in which at least a part of the component is disposed outside the corresponding region corresponding thereto also corresponds to the case of the above-mentioned "mainly disposed" as long as the majority of the component is included in the corresponding region corresponding thereto. A case where a description is made using "mainly disposed" in the following description also has the same meanings as described above.

Even in a case where the observation window 46 is mainly disposed in the distal end surface region 40A and the first treatment tool outlet port 52 is mainly disposed in the distal end surface region 40B in this way, the high-frequency forceps 100 can be observed as an image facing the lesion area 300, which is positioned at the center of the screen, from the lower side of the biological image 400. Accordingly, treatment using the high-frequency forceps 100 can be performed accurately. However, in a case where the endoscope has configuration in which the observation window 46 is completely included in the distal end surface region 40A and the first treatment tool outlet port 52 is completely included in the distal end surface region 40B, treatment using the high-frequency forceps 100 can be performed accurately. Further, in a case where the observation window 46 is disposed in the first quadrant 70A and the first treatment tool outlet port 52 is disposed in the fourth quadrant 70D, the high-frequency forceps 100 can be observed as an image facing the lesion area 300, which is positioned at the center of the screen, from the position of about 6 o'clock on the lower side in the screen. Accordingly, treatment using the high-frequency forceps 100 can be performed more accurately.

An aspect in which the front water supply port 56 is disposed to completely deviate from the line L1 to the outer periphery 40C has been described in the embodiment as a preferred aspect, but the present invention is not limited thereto. At least the center 56A of the front water supply port 56 may deviate from the line L1 to the outer periphery 40C. That is, the same effects as those of the embodiment can be obtained even in an aspect in which the center 56A of the front water supply port 56 is disposed at a position deviating from the line L1 to the outer periphery 40C.

Further, it is preferable that the front water supply port 56 is mainly disposed in the fourth quadrant 70D in the above-mentioned offset disposition. In this case, the liquid 60 jetted from the front water supply port 56 is observed as an image facing the lesion area 300, which is positioned at the center of the screen, from the position of 7 to 8 o'clock on the lower left side in the screen. Accordingly, even in this case, it is easy to see whether or not the liquid 60 jetted from the front water supply port 56 is accurately sprayed on the lesion area.

The endoscope 10 according to the embodiment described above is an endoscope that includes the first treatment tool outlet port 52 and the second treatment tool outlet port 54, but the first treatment tool outlet port 52 may be mainly disposed in the third quadrant 70C in the case of an endoscope that includes only the first treatment tool outlet port 52 as a treatment tool outlet port. In this case, the high-frequency forceps 100 is observed as an image facing the lesion area 300, which is positioned at the center of the screen from the position of 4 to 5 o'clock on the lower right in the screen. Accordingly, in a case where an operator performs treatment while observing the lesion area 300 in the biological image 400, the high-frequency forceps 100 do not serve as an obstacle and the operator can accurately perform treatment, which uses the high-frequency forceps 100, while observing the lesion area 300.

The specific arrangement form of the observation window 46, the first treatment tool outlet port 52, the second treatment tool outlet port 54, the front water supply port 56, the illumination windows 42 and 44, and the air/water supply nozzle 58 disposed on the distal end surface 40 shown in FIG. 2 will be described below with reference to FIG. 2.

First, the first treatment tool outlet port 52 is disposed at a position below the observation window 46, and the second treatment tool outlet port 54 is disposed at a position below the observation window 46 and on the lateral side of the first treatment tool outlet port 52. Specifically, the observation window 46 is disposed in the first quadrant 70A, the first treatment tool outlet port 52 is disposed in the fourth quadrant 70D, and the second treatment tool outlet port 54 is disposed in the third quadrant 70C. In a case where the above-mentioned arrangement relationship is satisfied, as shown in FIG. 7, the high-frequency forceps 100 are observed as an image facing the lesion area 300, which is positioned at the center of the screen, from the position of about 6 o'clock on the lower side in the screen and the grasping forceps 200 is observed as an image facing the lesion area 300, which is positioned at the center of the screen, from the position of 4 to 5 o'clock on the lower right side in the screen. That is, since the high-frequency forceps 100 and the grasping forceps 200 are displayed in the biological image 400 without overlapping with each other, the high-frequency forceps 100 and the grasping forceps 200 are easily seen. As a result, treatment, which uses the high-frequency forceps 100 and the grasping forceps 200, can be performed more accurately.

Further, since the grasping forceps 200 have multiple functions (bending function) as compared to the high-frequency forceps 100, the diameter of the grasping forceps 200 is larger than the diameter of the high-frequency forceps 100. For this reason, the second treatment tool outlet port 54 has a diameter larger than the diameter of the first treatment tool outlet port 52. Furthermore, since the second treatment tool outlet port 54 is disposed in the third quadrant 70C, an image region of the biological image 400, which is occupied by the image of the grasping forceps 200, can be reduced in size. Accordingly, since the high-frequency forceps 100 are more easily seen, treatment using the high-frequency forceps 100 can be performed accurately.

Moreover, the distal end surface 40 comprises a first surface 41A and a second surface 41B that protrudes in a direction (Y(+) direction) toward the distal end of the insertion unit 20 from the first surface 41A, the front water supply port 56 is disposed on the first surface 41A, and the observation window 46 is disposed on the second surface 41B. Here, the first surface 41A corresponds to a first surface of the present invention, and the second surface 41B corresponds to a second surface of the present invention. In this example, the second surface 41B having a fan shape in plan view is formed in the first quadrant 70A, and the first surface 41A is formed in a part of the first quadrant 70A, the second quadrant 70B, the third quadrant 70C, and the fourth quadrant 70D.

Since the observation window 46 is disposed on the second surface 41B and the front water supply port 56 is disposed on the first surface 41A, halation (a phenomenon in which an image becomes white), which is caused by the remaining water of the liquid 60 raised from the front water supply port 56 in the Y(+) direction, and the like can be suppressed. Specifically, when the liquid 60 has been completely supplied from the front water supply port 56, the remaining water of the liquid 60 is raised in the Y(+) direction at the opening of the front water supply port 56 due to the influence of the surface tension thereof. As a result, there is a concern that the raised remaining water may glare in the screen or halation may be caused by the reflection of applied light by the raised remaining water. In contrast, since the endoscope 10 according to the embodiment has configuration in which the observation window 46 is disposed on the second surface 41B and the front water supply port 56 is disposed on the first surface 41A, the glare of the remaining water caused by the raised remaining water and halation can be suppressed. As a result, a good image can be displayed.

Further, the illumination window 42 (first illumination window) is further disposed on the second surface 41B in the configuration in which the observation window 46 is disposed on the second surface 41B and the front water supply port 56 is disposed on the first surface 41A. Accordingly, it is possible to suppress that the remaining water of the front water supply port 56 adheres to the illumination window 42. As a result, a reduction in the amount of illumination light, which is caused by the adhesion of the remaining water to the illumination window 42, and halation can be suppressed.

The illumination window 44 corresponding to the second illumination window is disposed on the first surface 41A. The illumination window 44 is positioned on a side opposite to the side where the front water supply port 56 is disposed with the observation window 46 therebetween, and is disposed at a position farther from the front water supply port 56 than the illumination window 42. For this reason, since the remaining water of the front water supply port 56 is more difficult to adhere to the illumination window 44 than the illumination window 42, the illumination window 44 can be disposed on the first surface 41A. It goes without saying that the illumination window 44 may be disposed on the second surface 41B like the illumination window 42.

Further, the air/water supply nozzle 58 is disposed in the second quadrant 70B. Accordingly, the second quadrant 70B, which is empty in terms of a space, can be effectively used as an arrangement space for the air/water supply nozzle 58. As a result, the diameter of the distal end part 26 can be reduced.

Furthermore, the illumination window 44 (second illumination window) is disposed to be offset to the outer periphery 40C of the distal end surface 40 on a side opposite to the center C of the distal end surface 40 with respect to a line L2 connecting the center 46A of the observation window 46 to a center 58A of the air/water supply nozzle 58. The reason why this arrangement is desirable will be described below.

The bendable part 202 of the grasping forceps 200 led out of the second treatment tool outlet port 54 is bent upward as shown in FIG. 5. At this time, in a case where the illumination window 44 is disposed close to the second treatment tool outlet port 54, a part of light emitted from the illumination window 44 may be reflected by the pair of grasping parts 204, become scattered light, and be received by the image pickup element from the observation window 46, so that halation may occur. Since the endoscope 10 according to the embodiment has configuration in which the illumination window 44 is disposed to be offset to a position away from the second treatment tool outlet port 54 as described above, it is possible to suppress that the scattered light is received by the image pickup element. As a result, since it is possible to suppress halation that is caused by the grasping forceps 200 led out of the second treatment tool outlet port 54, a good image can be displayed.

An aspect in which the illumination window 44 is disposed to completely deviate from the line L2 to the outer periphery 40C has been described in the embodiment as a preferred aspect, but the present invention is not limited thereto. At least a center 44A of the illumination window 44 may deviate from the line L2 to the outer periphery 40C. That is, the same effects as those of the embodiment can be obtained even in an aspect in which the illumination window 44 is disposed at a position overlapping with the line L2.

Further, it is preferable that the illumination window 44 is disposed on the vertical axis V in the above-mentioned offset disposition. In this case, it is possible to suppress that illumination light emitted from the illumination window 44 is blocked by the pair of grasping parts 204 even though the bendable part 202 of the grasping forceps 200 is bent. As a result, a bright and good image can be displayed.

An aspect in which the center 44A of the illumination window 44 is disposed at a position overlapping with the vertical axis V has been described in the embodiment as a preferred aspect, but the present invention is not limited thereto. At least a part of the illumination window 44 may be disposed on the vertical axis V. That is, the same effects as those of the embodiment can be obtained even in an aspect in which a part of the illumination window 44 is disposed on the vertical axis V.

The endoscope 10, which comprises two treatment tool outlet ports (the first treatment tool outlet port 52 and the second treatment tool outlet port 54) on the distal end surface 40 has been described in the above-mentioned embodiment, but the present invention can be applied to even an endoscope that comprises only the first treatment tool outlet port. That is, in a case where the observation window 46 is disposed in the distal end surface region 40A positioned above the horizontal axis H and the first treatment tool outlet port 52 is disposed in the distal end surface region 40B positioned below the horizontal axis H on the distal end surface 40, a treatment tool is observed as an image facing the central portion of the biological image from the lower side of the biological image. Accordingly, treatment using the treatment tool can be performed accurately.

Several preferred aspects related to the endoscope 10 according to the embodiment will be described below.

As for Adjustment of Mounting Position of Observation Window

First, a case where the first treatment tool outlet port 52 is disposed immediately below the observation window 46 in the direction of the vertical axis V will be described. The lead-out position of the treatment tool to be observed in an observation image is changed in the observation image depending on the mounting position of the observation window 46. An example thereof will be described with reference to FIG. 8.

Reference numeral VIIIA of FIG. 8 denotes an observation image 502 that is obtained in a case where a line (not shown) connecting the center 46A of the observation window 46 (that is, the center of the observation optical system) to the center 52A (see FIG. 2) of the first treatment tool outlet port 52 is inclined to the right from a line parallel to the vertical axis V by an angle of 1° or less as the distal end surface 40 is viewed in the Y(+) direction. Reference numeral VIIIB denotes an observation image 504 that is obtained in a case where a line connecting the center 46A of the observation window 46 to the center 52A of the first treatment tool outlet port 52 is inclined to the right from a line parallel to the vertical axis V by an angle of 10° as the distal end surface 40 is viewed in the Y(+) direction. Reference numeral VIIIC denotes an observation image 506 that is obtained in a case where a line connecting the center 46A of the observation window 46 to the center 52A of the first treatment tool outlet port 52 is inclined to the left from a line parallel to the vertical axis V by an angle of 7° as the distal end surface 40 is viewed in the Y(+) direction. For convenience of description, the aspect of a case where the center 46A of the observation window 46 and the center of the observation optical system are aligned with each other on the same straight line in advance will be described in this example, but the position of the center of the observation optical system shall be adjusted in a case where the center 46A of the observation window 46 and the center of the observation optical system are not aligned with each other.

The high-frequency forceps 100 are observed in the observation image 502 so as to be led from the lower portion (the position of 6 o'clock) of the observation image 502 to the center of the observation image 502. In contrast, the high-frequency forceps 100 are observed in the observation image 504 so as to be led from the lower left of the observation image 504, and are observed in the observation image 506 so as to be led from the lower right of the observation image 506.

As described above, the high-frequency forceps 100 are seemed to be led from different positions in the observation image depending on the mounting position of the observation window 46. For this reason, there is a possibility that an operator's technique is affected.

Accordingly, in order to solve such a problem, the mounting position of the observation window 46 is adjusted and the inclination of a line connecting the center 46A of the observation window 46 to the center 52A of the first treatment tool outlet port 52 is set within 3° from the vertical axis V so that the lead-out position of the high-frequency forceps 100 in the observation image is seen constant. Therefore, an operator can perform treatment with a stable technique.

As a method of adjusting the mounting position of the observation window 46, an operator can adjust the position of the observation window 46 using an adjustment jig while looking at an image picked up by the observation optical system.

As for Bending Operation Mechanism

Next, an example of a bending operation mechanism for bending the bendable part 24 among the components of the hand operation unit 18 will be described. FIG. 9 is a schematic cross-sectional view of the hand operation unit 18, and a part of the bendable part 24 is also shown as a cross-sectional view in FIG. 9. Further, a bending operation mechanism, which bends the bendable part 24 in the up/down direction, of bending operation mechanisms for bending the bendable part 24 is shown in FIG. 9, and a bending operation mechanism for bending the bendable part 24 in the left/right direction will not be shown since being the same mechanism. The former bending operation mechanism will be described below and the description of the latter bending operation mechanism will be omitted.

As shown in FIG. 9, for example, the bendable part 24 includes a plurality of substantially cylindrical bending pieces 552 and a plurality of rivet pins 554 connecting adjacent bending pieces 552, and adjacent bending pieces 552 are connected to each other to move rotationally about the rivet pins 554 as an axis.

Meanwhile, for example, as shown in FIGS. 12 to 14, a pair of angle wires 556 used to bend the bendable part 24 upward and downward and a pair of angle wires 556 used to bend the bendable part 24 leftward and rightward are inserted into the soft part 22 and the bendable part 24 in addition to built-in components, such as a first treatment tool channel 714, a second treatment tool channel 716, a liquid feed tube 708, a liquid supply tube 710, a gas supply tube 712, a signal cable 702, and light guides 704 and 706. The two pairs of angle wires 556 are disposed along the direction of the major axis Ax of the insertion unit 20, and are engaged with the bending pieces 552 by being inserted into holes 720 of pins 722a, 722b, 722c, and 722d provided inside each of the rivet pins 554 of the bendable part 24.

Further, each of the distal end portions of the pair of angle wires 556 for operation in the up/down direction of the two pairs of angle wires 556 is fixed to the distal end part 26, and the proximal end portions of the pair of angle wires 556 are joined to a pair of sleeves 557 for operation in the up/down direction shown in FIG. 9, respectively. Accordingly, in a case where the pair of angle wires 556 are operated to be pushed and pulled through the pair of sleeves 557, the bendable part 24 is bent in the up/down direction.

The bending operation mechanism 558 for operation in the up/down direction, which is provided in the hand operation unit 18, includes a sprocket 560 and a chain 562 wound around the sprocket 560. The pair of sleeves 557 is joined to both end portions of the chain 562.

The sprocket 560 is connected to the angle knob 28 for operation in the up/down direction (see FIG. 1) through a rotating shaft 560A, and is rotated with an operation for rotating the angle knob 28. Accordingly, the pair of angle wires 556 is operated to be pushed and pulled through the chain 562 and the pair of sleeves 557. That is, one of the pair of angle wires 556 is pulled to the proximal end side, and the other thereof is sent to the distal end side.

Here, stoppers 564A and 564B, which restrict the movement of the sleeves 557 and 557 to the proximal end side by coming into contact with the sleeves 557 and 557, are provided on the proximal end side of the sleeves 557 and 557. The positions of the stoppers 564A and 564B are adapted to be adjustable respectively, and the movement of the sleeves 557 and 557 is restricted by the stoppers 564A and 564B. As a result, the maximum bending angle of the bendable part 24 in the up/down direction is determined.

Further, with regard to the stoppers 564A and 564B, the position of the stopper 564A, which restricts the movement of the sleeve on the upper side (Z(+)side), is set on the proximal end side of the position of the stopper 564B, which restricts the movement of the sleeve on the lower side (Z(−)side). Accordingly, the bendable part 24 is bent at an upward angle larger than a downward angle. As a result, in a case where the bendable part 24 is bent upward, a body wall on a side opposite to the insertion direction of the insertion unit 20 can be observed. In this case, the downward bending angle is reduced (for example, a bending angle on the upper side is 210° but a bending angle on the lower side is 90°). However, since the upper side is mainly used in the endoscope, there is no problem with the use of the endoscope.

Meanwhile, even though the angle knob 28 is operated in an endoscope (for example, an endoscope simultaneously using two treatment tools) that requires a large pulling force (large torque) in a case where the bendable part 24 is to be bent, the angle wire 556 may not contribute to an operation for bending the bendable part 24 since the angle wire 556 has been elongated. In order to prevent this problem, the position of the stopper 564A, which restricts the movement of the sleeve on the upper side, is disposed closer to the proximal end. As a result, since the angle wire 556 including the amount of elongation of the angle wire 556 can be pulled, the bendable part can be bent upward even in the endoscope requiring large torque. In a case where the positions of the stoppers 564A and 564B are adjusted depending on the magnitude of torque in this way, it is possible to use common components without using dedicated components depending on the magnitude of the torque.

As for Bendable Part

Figure 10:
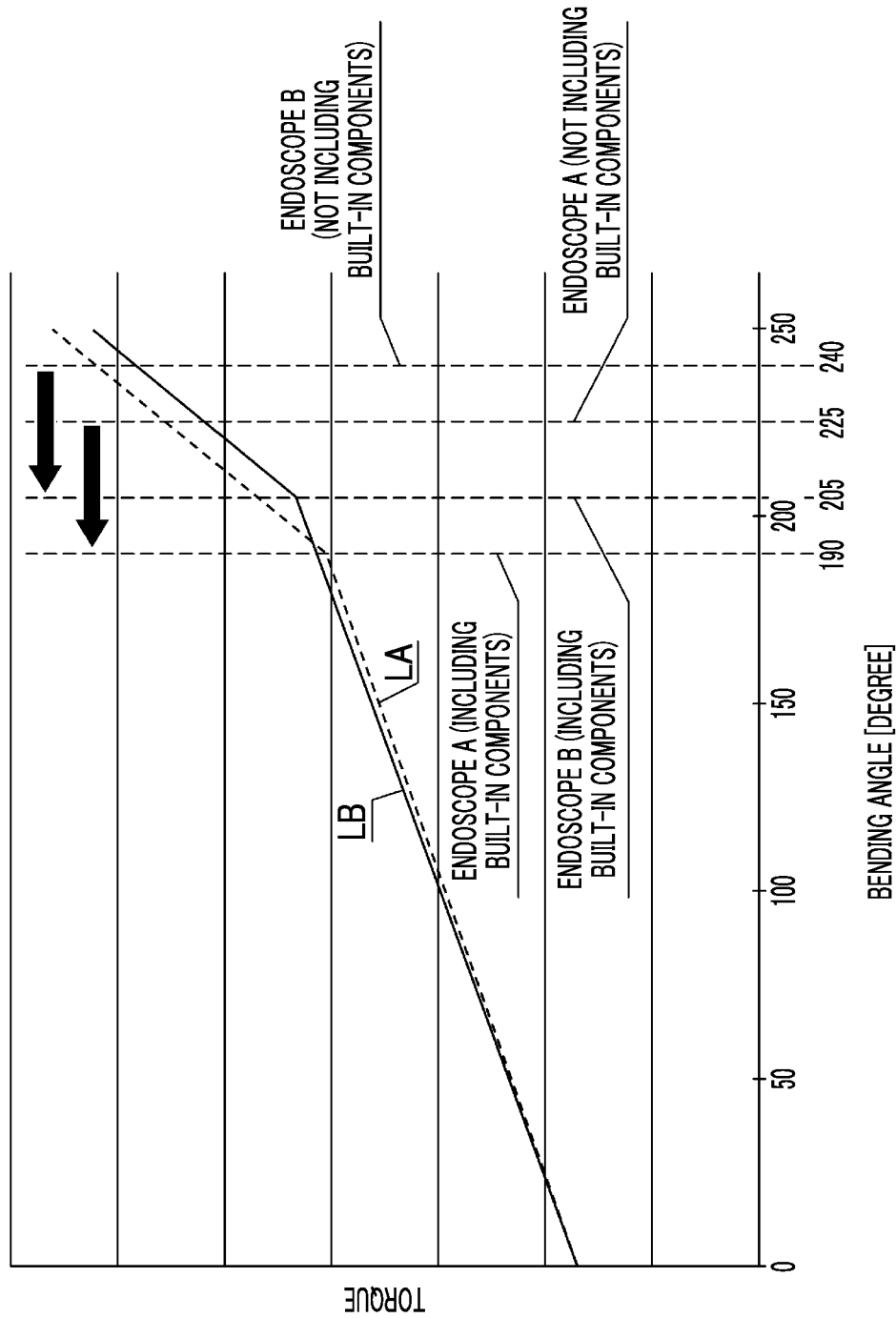
FIG. 10 is a diagram showing a relationship between torque, which is generated in a case where the bendable part is bent, and the bending angle of the bendable part.
Figure 11:
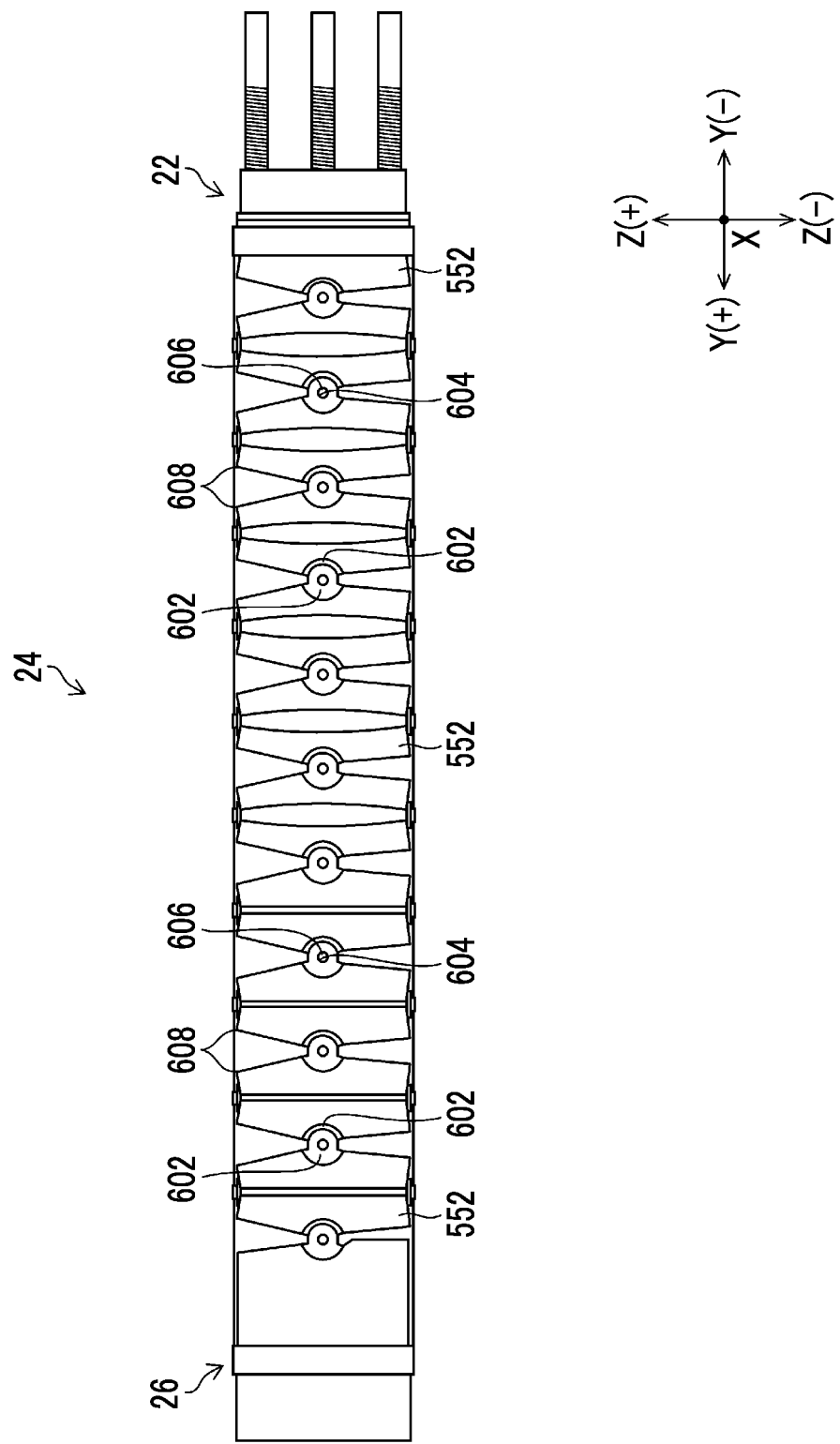
FIG. 11 is a diagram showing the connection state of a plurality of bending pieces that form the bendable part.

Next, an example of the configuration of the bendable part 24 will be described. FIG. 10 is a diagram (graph) showing a relationship between torque (pulling force), which is generated in a case where the bendable part 24 is to be bent, and the bending angle of the bendable part 24. FIG. 11 is a diagram showing the connection state of the plurality of bending pieces 552 of the bendable part 24.

In an endoscope having a torque fluctuation shown by a line LA of FIG. 10 (here, referred to as an endoscope A), the bendable part 24 can be bent with torque that gradually increases up to a certain angle. However, the endoscope has a point of inflection at which larger torque is required in a case where a bending angle exceeds a certain bending angle (190° in the case of the line LA). Accordingly, in this endoscope A, an operation for bending the bendable part 24 is performed without any problem in a case where a bending angle increases up to 190°. However, since larger torque is required in a case where a bending angle exceeds 190°, a load is applied on an operator. Further, since the angle wire 556 may be elongated even though the operator pulls the angle wire with large torque, a predetermined bending angle may not be capable of being obtained from the pulling force.

The line LA is measured in a state where the built-in components are included in the bendable part, but the tendency of the line LA is the same even in a state where the built-in components are not included. Accordingly, in a case where torque and a bending angle are measured with the bendable part alone, which does not include built-in components, in the endoscope A, it has been confirmed that the bendable part has a point of inflection at an angle of 225°.

Here, the bendable part 24 has configuration to be described below and an angle at a point of inflection in a state where built-in components are not included in the bendable part 24 is set to be larger than 225° to solve the above-mentioned problem. The configuration of the bendable part 24 will be described below.

That is, as shown in FIG. 11, a pair of connecting pieces 602 formed in the shape of a tongue is provided on each bending piece 552 of the bendable part 24 in a circumferential direction and protrudes from each bending piece 552 in the Y-axis direction. The pair of connecting pieces 602 is disposed at intervals of 180° in the circumferential direction of the bending piece 552. The connecting pieces 602 of adjacent bending pieces 552 overlap with each other and rivet pins 606 are mounted on through-holes 604 formed in the connecting pieces 602, so that the adjacent bending pieces 552 are connected to each other. Accordingly, the plurality of bending pieces 552 are connected to each other to move rotationally in the up/down direction through two rivet pins 606 and 606 that are provided in the left/right direction.

For example, the following can be performed in order to set the bending angle of the bendable part 24 to an angle larger than that in the related art. That is, an inclination angle of an end portion 608 with respect to the Z axis is set to be large so that end portions 608 and 608 of the adjacent bending pieces 552 facing each other in the Y-axis direction are away from each other in the Y-axis direction. Accordingly, in a case where the bendable part 24 is bent, the bending angle of the bendable part 24 is larger than that in the related art. As a result, the point of inflection of the bendable part 24 alone can be set to, for example, 225° or more, and the point of inflection of the bendable part 24 including the built-in components can be set to, for example, 205° or more (see an endoscope B shown by a line LB of FIG. 10).

It is preferable that intermediate bending pieces 552, which exclude a distal end-side bending piece 552 connected to the distal end part 26 and a proximal end-side bending piece 552 connected to the soft part 22, are applied as a bending piece having a large inclination angle of the end portion 608 among the plurality of bending pieces 552 connected to each other in the Y-axis direction.

That is, the position of the distal end-side bending piece 552 in the Y-axis direction is a position at which a tube as the sheath of the bendable part 24 is fixed to the distal end part 26, and is a portion at which stiffness is high since an adhesive is hardened. Accordingly, since large torque is required in order to bend this portion (a portion at which stiffness is high) in a case where the inclination angle of the end portion 608 is set to be large in the distal end-side bending piece 552, it is preferable that a bending piece in the related art is applied as the distal end-side bending piece 552.

Further, the position of the proximal end-side bending piece 552 in the Y-axis direction is a position that serves as the starting point of bending of the bendable part 24. Accordingly, in a case where the inclination angle of the end portion 608 is set to be large in the proximal end-side bending piece 552, the distal end part 26 of the endoscope 10 is raised high at the position of the bending piece 552. For this reason, a curvature obtained in a case where the bendable part 24 is bent is reduced, so that it is difficult to invert the bendable part 24 with a large curvature. That is, since the observation range of the endoscope 10 is narrowed, it is preferable that a bending piece in the related art is applied as the proximal end-side bending piece 552.

As for Internal Structure of Bendable Part

Next, the preferred internal structure of the bendable part 24 will be described. The illumination windows 42 and 44, the observation window 46, the first treatment tool outlet port 52, the second treatment tool outlet port 54, the air/water supply nozzle 58, and the front water supply port 56 are disposed on the distal end surface 40 of the endoscope 10 as described above. These are connected to the hand operation unit 18 through various cables and various channels (hereinafter, referred to as built-in components) that are inserted into the bendable part 24 and the soft part 22.

The illumination windows 42 and 44, the observation window 46, the first treatment tool outlet port 52, the second treatment tool outlet port 54, the air/water supply nozzle 58, and the front water supply port 56 are fixed to the distal end part 26. However, since the bendable part 24 is to be bent, it is preferable that the built-in components provided in the bendable part 24 are disposed without being fixed.

Incidentally, in a case where an operation for bending the bendable part 24 is repeated, the built-in components may be moved in the bendable part 24. In this case, there may be problems that the built-in components kink (are entangled or twisted), the cables are disconnected, the arrangement of the built-in components in the bendable part is disturbed with respect to the arrangement of the components on the distal end surface, and the like.

Accordingly, it is preferable that the endoscope has the following configuration to prevent the arrangement of the built-in components provided in the bendable part 24 from being disturbed.

(1) The outer diameters of the first treatment tool channel 714 and the second treatment tool channel 716 are increased.

FIG. 12 is a cross-sectional view showing the internal structure of the bendable part, and is a view of the bendable part viewed in the Y(+) direction from the Y(−) direction. In a case where the inside of the bendable part 24 is divided in half in the Z-axis direction according to the arrangement of the respective components on the distal end surface 40, the signal cable 702, the light guides 704 and 706, the liquid feed tube 708 for feeding water to the front water supply port 56, the liquid supply tube 710 for supplying liquid to the air/water supply nozzle 58, and the gas supply tube 712 for supplying gas to the air/water supply nozzle 58 are disposed in a region, which corresponds to the Z(+) direction, of the divided two regions. Further, the first treatment tool channel 714 and the second treatment tool channel 716 are disposed in a region corresponding to the Z(−) direction. Furthermore, pins 722*a*, 722*b*, 722*c*, and 722*d*, which include holes 720 into which the angle wires 556 used to bend the bendable part 24 are to be inserted, are provided on the upper, lower, left, and right sides on the inner periphery of the bendable part 24.

In the bendable part 24 shown in FIG. 12, the outer diameter of each of the first treatment tool channel 714 and the second treatment tool channel 716 is set to be large and a distance between the pins 722*b* and 722*d* facing each other in the X-axis direction is set to be shorter than the sum of the outer diameter of the first treatment tool channel 714 and the outer diameter of the second treatment tool channel 716.

In addition, it is preferable that the first treatment tool channel 714 has an outer diameter allowing the first treatment tool channel 714 not to move to a region corresponding to the Z(+) direction by allowing the first treatment tool channel 714 to be in contact with the pin 722*d* provided on the X(−) side and the second treatment tool channel 716, and the second treatment tool channel 716 has an outer diameter allowing the second treatment tool channel 716 not to move to a region corresponding to the Z(+) direction by allowing the second treatment tool channel 716 to be in contact with the pin 722b provided on the X(+) side and the first treatment tool channel 714.

According to the above-mentioned configuration, it is possible to prevent both the first treatment tool channel 714 and the second treatment tool channel 716 from moving to the region corresponding to the Z(+) direction. Further, it is possible to prevent the signal cable 702, the light guides 704 and 706, the liquid feed tube 708, the liquid supply tube 710, and the gas supply tube 712 from moving to the region corresponding to the Z(−) direction by the first treatment tool channel 714 and the second treatment tool channel 716. As a result, it is possible to prevent the arrangement of the built-in components provided in the bendable part 24 from being disturbed.

(2) The pins extend toward the central portion.

FIG. 13 is a diagram illustrating another embodiment that prevents the disturbance of the arrangement. In the embodiment shown in FIG. 13, pins 722b and 722d provided to face each other in the X-axis direction extend toward the center of the bendable part 24. Further, a distance between the pins 722b and 722d facing each other is set to be shorter than the outer diameter of the first treatment tool channel 714 and the outer diameter of the second treatment tool channel 716.

Accordingly, it is possible to prevent the first treatment tool channel 714 and the second treatment tool channel 716 from moving to a region corresponding to the Z(+) direction from the pins 722d and 722b provided in the X-axis direction. As a result, it is possible to prevent the arrangement of the built-in components provided in the bendable part 24 from being disturbed.

Further, since a force applied to the pins 722b and 722d can be dispersed in a case where the shapes of the pins 722b and 722d of each bending piece 552 of the bendable part 24 are set to the above-mentioned shapes, it is possible to prevent the pins 722b and 722d from being damaged.

(3) A partition member is provided in the bendable part.

FIG. 14 is a diagram illustrating still another embodiment that prevents the disturbance of the arrangement. In the embodiment shown in FIG. 14, a partition member 724 is provided in a region corresponding to the Z(+) direction. The partition member 724 is a component that is housed in the region corresponding to the Z(+) direction, and is provided to surround the signal cable 702, the light guides 704 and 706, the liquid feed tube 708, the liquid supply tube 710, and the gas supply tube 712.

Accordingly, it is possible to prevent various cables and various channels from being exchanged between the region corresponding to the Z(+) direction and the region corresponding to the Z(−) direction. As a result, it is possible to prevent the arrangement of the built-in components from being disturbed.

A position where the partition member 724 is provided can be provided at any position in the bendable part 24. The partition member 724 can be installed by a method including fixing the partition member 724 by spot welding, assembling the bendable part, and inserting the partition member into the bendable part for assembly.

The endoscope according to the embodiment has been described above, but the present invention may include some improvements or modifications without departing from the scope of the present invention.

EXPLANATION OF REFERENCES

10: endoscope
12: endoscope system
14: processor device for endoscope
16: display
18: hand operation unit
20: insertion unit
22: soft part
24: bendable part
26: distal end part
28: angle knob
30: angle knob
31A: air/water supply button
31B: suction button
32: universal cable
34: connector device
35: water supply connector
36: light source device
37: processor-side connector
38: image processing device
40: distal end surface
40A: upper distal end surface region
40B: lower distal end surface region
40C: outer periphery
41A: first surface
41B: second surface
42: illumination window
44: illumination window
44A: center
46: observation window
46A: center
48: first treatment tool inlet port
50: second treatment tool inlet port
52: first treatment tool outlet port
52A: center
54: second treatment tool outlet port
54A: center
56: front water supply port
56A: center
58: air/water supply nozzle
58A: center
60: liquid
70A: first quadrant
70B: second quadrant
70C: third quadrant
70D: fourth quadrant
100: high-frequency forceps
102: claw
200: grasping forceps
202: bendable part
204: grasping part
300: lesion area
400: biological image
502: observation image
504: observation image
506: observation image
552: bending piece
554: rivet pin
556: angle wire
557: sleeve
558: bending operation mechanism
560: sprocket
560A: rotating shaft
562: chain
564A: stopper
564B: stopper
602: connecting piece
604: through-hole
606: rivet pin
608: end portion 702: signal cable
704: light guide
706: light guide
708: liquid feed tube
710: liquid supply tube
712: gas supply tube
714: first treatment tool channel
716: second treatment tool channel
720: hole
722a: pin
722b: pin
722c: pin
722d: pin
724: partition member
H: horizontal axis
V: vertical axis
L1: line
L2: line
LA: line
LB: line
Ax: major axis
C: center

What is claimed is:

1. An endoscope comprising:
an observation window that is provided on a distal end surface of an insertion unit bendable in an up/down direction and a left/right direction and is used to observe an inside of an object to be examined;
a first treatment tool outlet port provided on the distal end surface and configured to accommodate a first treatment tool;
a second treatment tool outlet port provided on the distal end surface and configured to accommodate a second treatment tool; and
a front water supply port that is provided on the distal end surface and jets liquid to a portion to be observed in the object to be examined,
wherein as the distal end surface is viewed from a front, a first axis and a second axis passing through a center of the distal end surface are orthogonal to each other, the first axis is parallel to the left/right direction, the second axis is parallel to the up/down direction, a center of the observation window is positioned above the first axis, a center of the first treatment tool outlet port is positioned below the first axis, and a center of the front water supply port is positioned between the center of the observation window and the center of the first treatment tool outlet port in the direction of the second axis,
wherein the center of the front water supply port is positioned between the center of the observation window and a center of the second treatment tool outlet port in the direction of the second axis,
wherein an up direction of the endoscope corresponds to an up direction of an image based on electrical signals from an image pickup element of the endoscope,
wherein in the second axis direction, the center of the second treatment tool outlet port is disposed above the center of the first treatment tool outlet port.

2. The endoscope according to claim 1,
wherein in a case where, among four divided regions into which the distal end surface is divided by the first axis and the second axis, an upper right divided region is defined as a first quadrant, an upper left divided region is defined as a second quadrant, a lower left divided region is defined as a third quadrant, and a lower right divided region is defined as a fourth quadrant, the observation window is disposed in the first quadrant and the center of the first treatment tool outlet port is disposed in the fourth quadrant or the third quadrant.

3. The endoscope according to claim 2,
wherein the front water supply port is disposed on a side opposite to the center of the distal end surface with respect to a line connecting the center of the observation window to the center of the first treatment tool outlet port, and is disposed adjacent to an outer periphery of the distal end surface.

4. The endoscope according to claim 3,
wherein the front water supply port is disposed in the fourth quadrant.

5. The endoscope according to claim 2, further comprising:
wherein the first treatment tool outlet port is entirely disposed in the fourth quadrant, and
the second treatment tool outlet port is entirely disposed in the third quadrant.

6. The endoscope according to claim 5,
wherein the second treatment tool outlet port has a diameter larger than a diameter of the first treatment tool outlet port.

7. The endoscope according to claim 1,
wherein the distal end surface includes a first surface and a second surface that protrudes in a direction toward a distal end of the insertion unit from the first surface,
the front water supply port is disposed on the first surface, and
the observation window is disposed on the second surface.

8. The endoscope according to claim 7, further comprising:
a first illumination window that is provided on the second surface.

9. The endoscope according to claim 1,
wherein in a case where, among four divided regions into which the distal end surface is divided by the first axis and the second axis, an upper right divided region is defined as a first quadrant, an upper left divided region is defined as a second quadrant, a lower left divided region is defined as a third quadrant, and a lower right divided region is defined as a fourth quadrant, an air/water supply nozzle is provided in the second quadrant.

10. The endoscope according to claim 9, further comprising:
an illumination window that is provided on the distal end surface,
wherein the illumination window is disposed on a side opposite to the center of the distal end surface with respect to a line connecting the center of the observation window to a center of the air/water supply nozzle, and is disposed adjacent to an outer periphery of the distal end surface.

11. The endoscope according to claim 10,
wherein the illumination window is disposed on the second axis.

12. The endoscope according to claim 1,
wherein in the first axis direction, the center of the second treatment tool outlet port, the center of the first treatment tool outlet port, and the front water supply port are arranged in that order.

13. An endoscope system comprising:
an endoscope that has an image pickup element; and a processor device that is configured to display, on a screen, an image based on electrical signals from the image pickup element:

wherein the endoscope comprises:

an observation window that is provided on a distal end surface of an insertion unit bendable in an up/down direction and a left/right direction and is used to observe an inside of an object to be examined;

a first treatment tool outlet port provided on the distal end surface and configured to accommodate a first treatment tool;

a second treatment tool outlet port provided on the distal end surface and configured to accommodate a second treatment tool; and a front water supply port that is provided on the distal end surface and jets liquid to a portion to be observed in the object to be examined, wherein as the distal end surface is viewed from a front, a first axis and a second axis passing through a center of the distal end surface are orthogonal to each other, the first axis is parallel to the left/right direction, the second axis is parallel to the up/down direction, a center of the observation window is positioned above the first axis, a center of the first treatment tool outlet port is positioned below the first axis, and a center of the front water supply port is positioned between the center of the observation window and the center of the first treatment tool outlet port in the direction of the second axis, wherein the up/down direction is aligned with a vertical direction of the image displayed on the screen, wherein an up direction of the endoscope corresponds to an up direction of an image based on electrical signals from an image pickup element of the endoscope, wherein in the second axis direction, the center of the second treatment tool outlet port is disposed above the center of the first treatment tool outlet port.

* * * * *